US00PP14381P39

(12) United States Plant Patent
Moore

(10) Patent No.: US PP14,381 P3
(45) Date of Patent: Dec. 16, 2003

(54) WEIGELA PLANT NAMED 'DARK HORSE'

(50) Latin Name: *Weigela florida*
Varietal Denomination: Dark Horse

(76) Inventor: Peter Robert Moore, 1 Valley View Longstock, Stockridge, Hampshire, England SO20 6EF (GB)

( * ) Notice: Subject to any disclaimer, the term of this patent is extended or adjusted under 35 U.S.C. 154(b) by 0 days.

(21) Appl. No.: 10/071,015

(22) Filed: Feb. 7, 2002

(65) Prior Publication Data

US 2003/0150031 P1 Aug. 7, 2003

(51) Int. Cl.[7] ..... A01H 5/00

(52) U.S. Cl. ..... Plt./226

(58) Field of Search ..... Plt./226

*Primary Examiner*—Anne Marie Grunberg

(57) ABSTRACT

A new cultivar of Weigela plant named 'Dark Horse' that is characterized by a compact habit, dark purple leaves and pink flowers that contrast with the dark foliage. In combination these traits set 'Dark Horse' apart from all other existing varieties of Weigela known to the inventor.

2 Drawing Sheets

Genus: Weigela.
Species: *florida.*
Denomination: Dark Horse.

BACKGROUND OF THE INVENTION

The present invention relates to a new and distinct cultivar of Weigela plant botanically known as *Weigela florida* and hereinafter referred to by the cultivar name 'Dark Horse'.

The new cultivar 'Dark Horse' is the product of a planned breeding program conducted by the inventor in Hampshire, England. The objective of the breeding program is to develop new plants with leaves that are darker than any existing Weigela. 'Dark Horse' is a hybrid that originated from an induced cross made by the inventor in 1991 using *Weigela florida* 'Victoria' (not patented) as the female or seed parent and *Weigela florida* 'Foliis Pupureus' (not patented) as the male or pollen parent. The new cultivar 'Dark Horse' was selected by the inventor in 1992 as a plant within the progeny of the stated cross in a controlled environment in Hampshire, England. The selection was made based on the dark purple foliage and compact habit.

The closest comparison plant is the dark-leaved, low-growing *Weigela florida* 'Foliis Purpureus' which exhibits a habit that becomes sprawling with age, and foliage color that fades toward the end of summer. Another comparison plant is Weigela 'Victoria', a tall dark-leaved shrub. 'Dark Horse' is distinguishable from *Wegelia florida* 'Foliis Purpureus' by its compact habit and foliage that remains dark purple throughout the plants season. 'Dark Horse' is distinguishable from 'Victoria' by its compact habit. The original Weigela 'Dark Horse' plant, belonging to the inventor, has retained its compact habit over the last eight years. Of the purple leaved forms 'Dark Horse' is the most compact variety known to the inventor.

Asexual reproduction by cuttings of the new cultivar 'Dark Horse' was accomplished in 1992 in Hampshire, England by the inventor. Since that time, under careful observation, the unique characteristics of the new Weigela plant have been uniform, stable and reproduced true to type in successive generations of asexual reproduction.

SUMMARY OF THE INVENTION

The following represent the distinguishing characteristics of the new Weigela cultivar 'Dark Horse'. These traits in combination distinguish 'Dark Horse' as a new and distinct cultivar apart from all other existing varieties of Weigela known to the inventor. 'Dark Horse' has not been tested under all possible conditions and phenotypic differences may be observed with variations in environmental, climatic, and cultural conditions, however, without any variance in genotype.

1. Weigela 'Dark Horse' exhibits dark purple leaves.
2. Weigela 'Dark Horse' exhibits a distinctly compact growth habit.
3. Weigela 'Dark Horse' is hardy to USDA Zone 4.
4. Weigela 'Dark Horse' is 62 cm. in height and 93 cm. in width at maturity.
5. The foliage of Weigela 'Dark Horse' remains dark purple throughout the plants season.
6. Weigelia 'Dark Horse' exhibits a floriferous display of pink flowers that contrast with the dark foliage.

BRIEF DESCRIPTION OF THE DRAWINGS

The accompanying color drawings illustrate the overall appearance of the new variety Weigela 'Dark Horse' showing colors as true as it is reasonably possible to obtain in colored reproductions of this type. Colors in the drawings may differ from the color values cited in the detailed botanical description which more accurately describe the actual colors of the new variety 'Dark Horse'. The plant in the drawings was grown in a two-gallon container under greenhouse conditions.

The drawing on sheet 1 illustrates the entire plant in bloom from a side perspective.

The drawing on sheet 2 is a close-up view of the flower. The drawings were made using conventional techniques and although colors may appear different from actual colors due to light reflectance, they are as accurate as possible by conventional photography.

BOTANICAL DESCRIPTION OF THE PLANT

The following is a detailed description of the Weigela cultivar named 'Dark Horse'. Data was collected in Arroyo Grande, Calif. from plants grown in two-gallon containers under greenhouse conditions. The decision was made to file this application before the next flowering cycle of the plants from which data was collected. Color determinations are in accordance with The Royal Horticultural Society Colour Chart except where general color terms of ordinary dictionary significance are used. The growing requirements are similar to the species and there are no disease problems known to the inventors.

Botanical classification: Weigela 'Dark Horse'.
Species: *florida*.
Use: Ornamental.
Parentage: 'Dark Horse' is a hybrid plant that resulted from the induced hybridization of the following parent plants:
- *Female parent.*—*Weigela florida* 'Victoria' (not patented).
- *Male parent.*—*Weigela florida* 'Foliis Purpureus' (not patented).

Vigor: Slow-growing.
Growth habit: Compact.
Suitable container size: 1–3 gallon containers.
Height: 25 cm. in height from soil level to top of plant.
Width: 40 cm. in width.
Hardiness: USDA Zone 4.
Propagation: The plant is propagated using vegetative cuttings.
Time to initiate roots: 5–6 weeks are required to produce roots on an initial cutting.
Crop time: One year to 18 months are required to produce a finished one-gallon container from a rooted cutting.
Root system: Fibrous.
Light: Plant in full sun or partial shade.
Soil: Plant in moist but well drained soil.
Type: Perennial shrub.
Seasonal interest: Pink flowers in spring and early summer.
Stem:
- *Branching habit.*—Basal upright branching.
- *Stem diameter.*—3 mm. in diameter.
- *Stem length.*—10–20 cm. in length.
- *Internode length.*—1–3 cm. between nodes.
- *Shape.*—Tetrahedral.
- *Surface.*—Mostly glabrous but puberulent on corners.
- *Branch color.*—187A.

Foliage:
- *Type.*—Deciduous.
- *Leaf arrangement.*—Opposite.
- *Leaf division.*—Simple.
- *Leaf margin.*—Serrate.
- *Leaf surfaces* (*adaxial and abaxial*).—Matte surface with slight puberulence on veins.
- *Vein pattern.*—Pinnate with veins depressed on adaxial surface and protruding on abaxial surface.
- *Vein color* (*abaxial and adaxial surfaces*).—144A.
- *Leaf shape.*—Oblanceolate with undulate margins and tortuous toward apex,
- *Leaf apex.*—Cirrose.
- *Leaf base.*—Attenuate.
- *Stipules.*—Present.
- *Stipule dimensions.*—2 mm. in length and 1 mm. in width.
- *Stipule color.*—187A.
- *Leaf attachment.*—Petiolate.
- *Petiole dimensions.*—6 mm. in length and 3 mm. in width.
- *Petiole color.*—144D.
- *Leaf length.*—5–7 cm. in length.
- *Leaf width.*—2–3 cm. in width.
- *Leaf color* (*adaxial surface*).—183A.
- *Leaf color* (*abaxial surface*).—A combination of 183D and 144A.

Flower:
- *Flower shape.*—Closest to funnelform.
- *Flower color.*—A combination of both 71C and 75C are individually present on each individual flower.
- *Flower dimensions.*—3.25 cm. in length and 2.50 cm. in diameter at the widest part.
- *Corolla tube dimensions.*—2.75 cm. in depth and 2 cm. in width.
- *Inflorescence.*—Corymb.
- *Flower form.*—Solitary.
- *Aspect.*—Flowers facing upward and outward.
- *Color of flower petal* (*abaxial surface*).—71C.
- *Color of flower petal* (*adaxial surface*).—75C.
- *Surface of petals (adaxial and abaxial).*—Puberulent.
- *Surface of corolla tube (inside and outside).*—Puberulent.
- *Color of corolla tube* (*inside*).—71C.
- *Color of corolla tube* (*outside*).—71C.
- *Petals.*—Five in number.
- *Fused or unfused.*—Fused.
- *Petal apex.*—Rounded.
- *Petal shape.*—Closest to obelliptic.
- *Petal dimensions.*—3.25 cm. in length and 0.75 cm. in width.
- *Bud color.*—71B.
- *Bud shape.*—Closest to Obovate.
- *Bud dimensions.*—2.75 cm. in length and 0.50 cm. in width.
- *Calyx shape.*—Tubular.
- *Number of sepals.*—Five in number.
- *Sepal color* (*abaxial and adaxial color).*—183C.
- *Sepal shape.*—Lanceolate.
- *Fused of unfused.*—Fused.
- *Sepal dimensions.*—8 mm. in length and 1 mm. in width.
- *Sepal apex.*—Acuminate.
- *Sepal surface* (*adaxial and abaxial*).—Pillose.
- *Flower fragrance.*—None observed.
- *Number of flowers.*—Approximately 15 open flowers at a time to one individual branch.
- *Lastingness of individual bloom.*—Approximately 5–7 days.
- *Persistent or self-cleaning.*—Self-cleaning.
- *Bloom time.*—Diurnal.
- *Blooming period.*—April through June.

Reproduction organs:
- *Stamens.*—Five in number.
- *Stamen shape.*—Filament adnate to inside of corolla tube.
- *Stamen dimensions.*—6 mm. in length and less than 1 mm. in width.
- *Stamen color.*—158C.

*Anther shape.*—Globular.
*Anther color.*—158C.
*Anther dimensions.*—0.50 mm. in length and 0.50 mm. in width.
*Amount of pollen.*—Moderate.
*Color of pollen.*—158C.
*Pistil.*—One.
*Pistil color.*—157D
*Pistil dimensions.*—3.00 cm. in length and 1.50 mm. in width.
*Stigma color.*—157D.
*Stigma shape.*—Globular.
*Stigma dimensions.*—2.75 mm. in diameter and 2.75 mm. in length.
*Stigma.*—Exserted.
*Style.*—One in number.
*Style shape.*—Slender filament.
*Style color.*—157D.
*Style measurements.*—1 mm. in width and 4 mm. in length.
*Ovary.*—Inferior.

Seed: Seed production was not observed to date.

I claim:

1. A new and distinct variety of Weigela plant named 'Dark Horse' as described and illustrated.

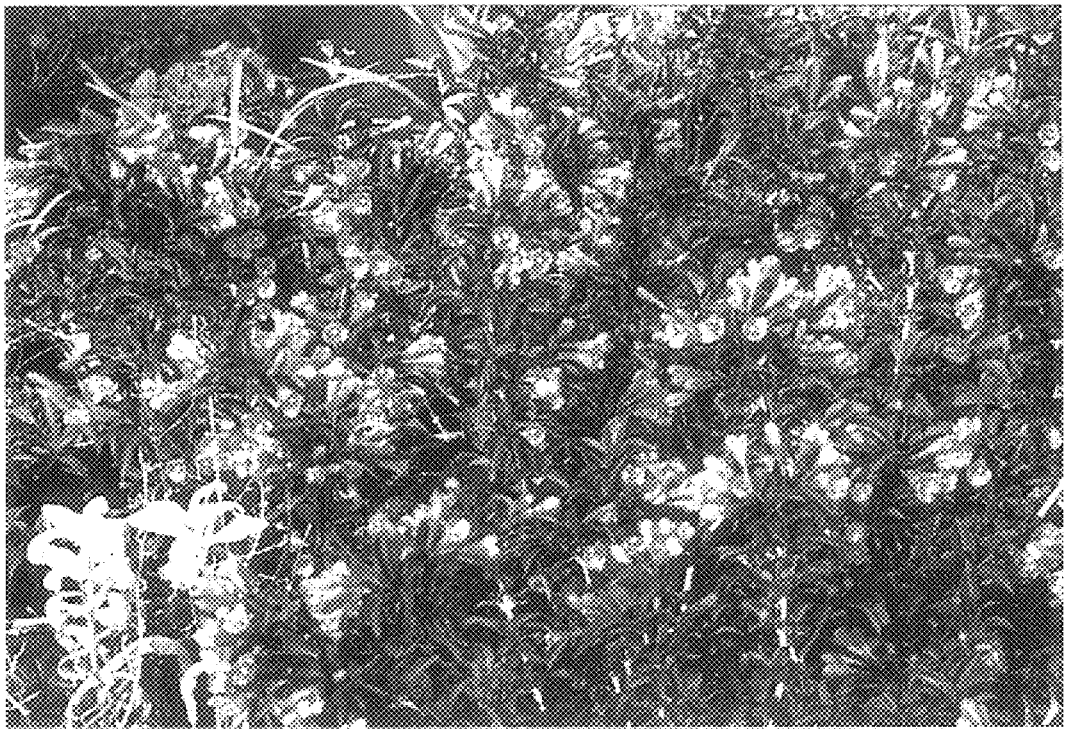

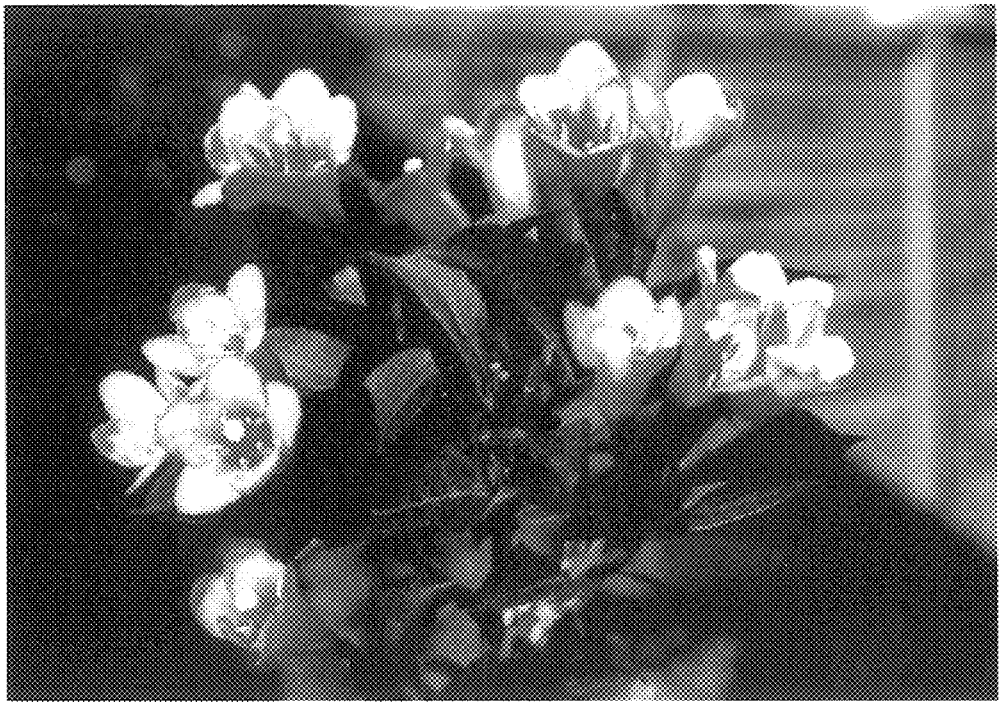

* * * * *